United States Patent
Teramoto

(10) Patent No.: US 10,550,398 B2
(45) Date of Patent: Feb. 4, 2020

(54) RLMA-INACTIVATED FILAMENTOUS FUNGAL HOST CELL

(71) Applicant: Novozymes A/S, Bagsvaerd (DK)

(72) Inventor: Hiroshi Teramoto, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/094,795

(22) PCT Filed: Apr. 18, 2017

(86) PCT No.: PCT/EP2017/059129
§ 371 (c)(1),
(2) Date: Oct. 18, 2018

(87) PCT Pub. No.: WO2017/182442
PCT Pub. Date: Oct. 26, 2017

(65) Prior Publication Data
US 2019/0119690 A1 Apr. 25, 2019

(30) Foreign Application Priority Data

Apr. 19, 2016 (EP) .................................... 16165997
Jun. 29, 2016 (EP) .................................... 16176897

(51) Int. Cl.
*C12N 15/80* (2006.01)
*C12N 9/34* (2006.01)

(52) U.S. Cl.
CPC .......... *C12N 15/80* (2013.01); *C12N 9/2428* (2013.01)

(58) Field of Classification Search
None
See application file for complete search history.

(56) References Cited

FOREIGN PATENT DOCUMENTS

WO    2004090155 A2    10/2004

OTHER PUBLICATIONS

Fiedler et al, 2014, Fungal biology and biotechnology 1, 1-16.
Damveld et al, 2005, Mol Microbiol 58, 305-319.

*Primary Examiner* — Brian Gangle
(74) *Attorney, Agent, or Firm* — Eric J. Fechter

(57) ABSTRACT

The present invention relates to RlmA-inactivated filamentous fungal cells secreting a polypeptide of interest and methods of producing a secreted polypeptide of interest in said cells as well as methods of producing said cells.

30 Claims, No Drawings

Specification includes a Sequence Listing.

SEQUENCE LISTING

<160> NUMBER OF SEQ ID NOS: 14

<210> SEQ ID NO 1
<211> LENGTH: 2032
<212> TYPE: DNA
<213> ORGANISM: Aspergillus niger

<400> SEQUENCE: 1

```
atgggtcgca gaaagatcga gatcaaggcg atcaaggatg atcgcaaccg ctcagtgtaa      60
gtgctaaagc tggtggatct cttcacctct cccattaaa ccctagttcg tcaagctaac      120
gctctggtgc gcgactagga cctttctgaa acggaagggt ggtctgttca agaaggcaca      180
tgagcttgcg gtcctgtgtt cggttgatgt cgctgttatt atctttggtc acaacaagaa      240
gctctacgaa ttctcgtcat gtgatatgcg agaggccctc actcgatatc aatacgtgcg      300
ttgtccacct aacccgctcg tctggaaaga ctgtcgttga tctgacattg ccgctttcct      360
atgcttttag tttggtcccc cacatgaaca caaaggccct gaagacttta acggcaaacg      420
cgacgatgat gatgacgaag atgagacgac gcctgccccc gaagatgtgc atcctacgcc      480
tccaaatcct cccatgattc ccgcccacct gccaggtcat cccggcttcc agcacgtcac      540
tcatgcgccg tctgcttccc cgcccatagg gaatgggatg gcatttgctc cgcgtcacgg      600
taccctcaa ccgcagggag tttctcggcc ttcgtctcgg aatcatcttc gtcgggtgag      660
ctccaatatg ggacctcaac agcatcacca tgcgaccccct ccgccgcctc cgccgccgcc      720
gcaaaatggc ttcacgtaca ttcctaatcc ttcggtatat aaccccaacg ctgctcacgc      780
catggctcaa cctccccgcc cacctcagtt cactcattac ggaccccccg ggccgcatca      840
ccaaccccct ccgcctccac agcatcatcc agcgatgccg ccacactcca tgccccccaca    900
gtctatgcct ccacatacaa tggcaccgca agccatgccg ccgcaccacc aggtcctcc      960
acacatgcca cacccgcctc atgcactttc acagcaaccg cctccaatgg ccatgaccca     1020
gccgccccat gccgccatcc cgcaggtcgc gcaagcgttt ctcccagagc aaggacgaaa     1080
ttccatgcct ccgacgttta caacagaaca gcaaccaccg ccgccacgaa cagtgtcgct     1140
tcctgaagga accgctccga cagacgcaat gccaggtccc atgaagacgg aaggaacccc     1200
atccccgccg caccagcgat ctctctcttc caagtctcgc agtatcttca cacccattga     1260
cgaccgaggc tccgtattgg cgcgccattt tggcgtaggt cctccgacgg aggcgggaga     1320
gaatgcgcaa acgaaggctg aaggagcaac actcggacca aacgaaggga agcctgctgg     1380
gctaactgca aagcccccctc ctccacctcc ccgagcggcc acggaagccc cgcgtcccca     1440
gccggtagtt gacctgaagc cgcctgtgcg tacaaacagc ggccagttcc cgcctaagcg     1500
cccgcagttg aaggtacaga taccgagtga gaattcggac cggggcagcg caacggcaga     1560
ttcatcgtca cgtgattctg cggggaacaa acgctcacg cctgccaaag cgaatccaga     1620
caccggtcac tcgagcgtgg tattgccccc gccctcgccg tctgcgggtg cgatattaag     1680
tgcagggggct caagggccgc caaatccttt gccccggcca ccgcctccgg gagcagcacc     1740
acagaacaac agtgcataca acaataatag caatatagat acgccaatct ctgctcttcc     1800
tagtcggttc gtctcggatg cgcttctccc gtcaccgtcc agtttctttc cggaatgggg     1860
ctttgggcgg tctggaccag acagcaacat gttgcccagt cccttgacgt tccctacgcc     1920
ggcggtacaa agtggccccg ggtttgggcg cgaggatgag caagacaaaa agcgcaaaag     1980
ccctgatagt ggacccaatg cggaaggggt agtgaagaaa ccaaagacgt aa             2032
```

<210> SEQ ID NO 2
<211> LENGTH: 1875
<212> TYPE: DNA
<213> ORGANISM: Aspergillus niger
<220> FEATURE:
<221> NAME/KEY: CDS
<222> LOCATION: (1)..(1872)
<223> OTHER INFORMATION: RlmA-encoding sequence

```
<400> SEQUENCE: 2 atg ggt cgc aga aag atc gag atc aag gcg atc aag gat gat cgc aac      48
Met Gly Arg Arg Lys Ile Glu Ile Lys Ala Ile Lys Asp Asp Arg Asn
1               5                   10                  15 cgc tca gtg acc ttt ctg aaa cgg aag ggt ggt ctg ttc aag aag gca      96
Arg Ser Val Thr Phe Leu Lys Arg Lys Gly Gly Leu Phe Lys Lys Ala
            20                  25                  30 cat gag ctt gcg gtc ctg tgt tcg gtt gat gtc gct gtt att atc ttt     144
His Glu Leu Ala Val Leu Cys Ser Val Asp Val Ala Val Ile Ile Phe
        35                  40                  45 ggt cac aac aag aag ctc tac gaa ttc tcg tca tgt gat atg cga gag     192
Gly His Asn Lys Lys Leu Tyr Glu Phe Ser Ser Cys Asp Met Arg Glu
    50                  55                  60 gcc ctc act cga tat caa tac ttt ggt ccc cca cat gaa cac aaa ggc     240
Ala Leu Thr Arg Tyr Gln Tyr Phe Gly Pro Pro His Glu His Lys Gly
65                  70                  75                  80 cct gaa gac ttt aac ggc aaa cgc gac gat gat gat gac gaa gat gag     288
Pro Glu Asp Phe Asn Gly Lys Arg Asp Asp Asp Asp Asp Glu Asp Glu
                85                  90                  95 acg acg cct gcc ccc gaa gat gtg cat cct acg cct cca aat cct ccc     336
Thr Thr Pro Ala Pro Glu Asp Val His Pro Thr Pro Pro Asn Pro Pro
            100                 105                 110 atg att ccc gcc cac ctg cca ggt cat ccc ggc ttc cag cac gtc act     384
Met Ile Pro Ala His Leu Pro Gly His Pro Gly Phe Gln His Val Thr
        115                 120                 125 cat gcg ccg tct gct tcc ccg ccc ata ggg aat ggg atg gca ttt gct     432
His Ala Pro Ser Ala Ser Pro Pro Ile Gly Asn Gly Met Ala Phe Ala
    130                 135                 140 ccg cgt cac ggt acc cct caa ccg cag gga gtt tct cgg cct tcg tct     480
Pro Arg His Gly Thr Pro Gln Pro Gln Gly Val Ser Arg Pro Ser Ser
145                 150                 155                 160 cgg aat cat ctt cgt cgg gtg agc tcc aat atg gga cct caa cag cat     528
Arg Asn His Leu Arg Arg Val Ser Ser Asn Met Gly Pro Gln Gln His
                165                 170                 175 cac cat gcg acc cct ccg ccg cct ccg ccg ccg caa aat ggc ttc         576
His His Ala Thr Pro Pro Pro Pro Pro Pro Pro Gln Asn Gly Phe
            180                 185                 190 acg tac att cct aat cct tcg gta tat aac ccc aac gct gct cac gcc     624
Thr Tyr Ile Pro Asn Pro Ser Val Tyr Asn Pro Asn Ala Ala His Ala
        195                 200                 205 atg gct caa cct ccc cgc cca cct cag ttc act cat tac gga ccc ccc     672
Met Ala Gln Pro Pro Arg Pro Pro Gln Phe Thr His Tyr Gly Pro Pro
    210                 215                 220 ggg ccg cat cac caa ccc cct ccg cct cca cag cat cat cca gcg atg     720
Gly Pro His His Gln Pro Pro Pro Pro Gln His His Pro Ala Met
225                 230                 235                 240 ccg cca cac tcc atg ccc cca cag tct atg cct cca cat aca atg gca     768
Pro Pro His Ser Met Pro Pro Gln Ser Met Pro Pro His Thr Met Ala
                245                 250                 255 ccg caa gcc atg ccg ccg cac cac cag gct cct cca cac atg cca cac     816
Pro Gln Ala Met Pro Pro His His Gln Ala Pro Pro His Met Pro His
            260                 265                 270 ccg cct cat gca ctt tca cag caa ccg cct cca atg gcc atg acc cag     864
Pro Pro His Ala Leu Ser Gln Gln Pro Pro Pro Met Ala Met Thr Gln
        275                 280                 285 ccg ccc cat gcc gcc atc ccg cag gtc gcg caa gcg ttt ctc cca gag     912
Pro Pro His Ala Ala Ile Pro Gln Val Ala Gln Ala Phe Leu Pro Glu
    290                 295                 300 caa gga cga aat tcc atg cct ccg acg ttt aca aca gaa cag caa cca     960
Gln Gly Arg Asn Ser Met Pro Pro Thr Phe Thr Thr Glu Gln Gln Pro
```

```
Gln Gly Arg Asn Ser Met Pro Pro Thr Phe Thr Thr Glu Gln Gln Pro
305                 310                 315                 320 ccg ccg cca cga aca gtg tcg ctt cct gaa gga acc gct ccg aca gac    1008
Pro Pro Pro Arg Thr Val Ser Leu Pro Glu Gly Thr Ala Pro Thr Asp
                325                 330                 335 gca atg cca ggt ccc atg aag acg gaa gga acc cca tcc ccg ccg cac    1056
Ala Met Pro Gly Pro Met Lys Thr Glu Gly Thr Pro Ser Pro Pro His
            340                 345                 350 cag cga tct ctc tct tcc aag tct cgc agt atc ttc aca ccc att gac    1104
Gln Arg Ser Leu Ser Ser Lys Ser Arg Ser Ile Phe Thr Pro Ile Asp
            355                 360                 365 gac cga ggc tcc gta ttg gcg cgc cat ttt ggc gta ggt cct ccg acg    1152
Asp Arg Gly Ser Val Leu Ala Arg His Phe Gly Val Gly Pro Pro Thr
        370                 375                 380 gag gcg gga gag aat gcg caa acg aag gct gaa gga gca aca ctc gga    1200
Glu Ala Gly Glu Asn Ala Gln Thr Lys Ala Glu Gly Ala Thr Leu Gly
385                 390                 395                 400 cca aac gaa ggg aag cct gct ggg cta act gca aag ccc cct cct cca    1248
Pro Asn Glu Gly Lys Pro Ala Gly Leu Thr Ala Lys Pro Pro Pro Pro
                405                 410                 415 cct ccc cga gcg gcc acg gaa gcc ccg cgt ccc cag ccg gta gtt gac    1296
Pro Pro Arg Ala Ala Thr Glu Ala Pro Arg Pro Gln Pro Val Val Asp
            420                 425                 430 ctg aag ccg cct gtg cgt aca aac agc ggc cag ttc ccg cct aag cgc    1344
Leu Lys Pro Pro Val Arg Thr Asn Ser Gly Gln Phe Pro Pro Lys Arg
            435                 440                 445 ccg cag ttg aag gta cag ata ccg agt gag aat tcg gac cgg ggc agc    1392
Pro Gln Leu Lys Val Gln Ile Pro Ser Glu Asn Ser Asp Arg Gly Ser
450                 455                 460 gca acg gca gat tca tcg tca cgt gat tct gcg ggg aac aaa acg ctc    1440
Ala Thr Ala Asp Ser Ser Ser Arg Asp Ser Ala Gly Asn Lys Thr Leu
465                 470                 475                 480 acg cct gcc aaa gcg aat cca gac acc ggt cac tcg agc gtg gta ttg    1488
Thr Pro Ala Lys Ala Asn Pro Asp Thr Gly His Ser Ser Val Val Leu
                485                 490                 495 ccc ccg ccc tcg ccg tct gcg ggt gcg ata tta agt gca ggg gct caa    1536
Pro Pro Pro Ser Pro Ser Ala Gly Ala Ile Leu Ser Ala Gly Ala Gln
            500                 505                 510 ggg ccg cca aat cct ttt gcc cgg cca ccg cct ccg gga gca gca cca    1584
Gly Pro Pro Asn Pro Phe Ala Arg Pro Pro Pro Pro Gly Ala Ala Pro
            515                 520                 525 cag aac aac agt gca tac aac aat aat agc aat ata gat acg cca atc    1632
Gln Asn Asn Ser Ala Tyr Asn Asn Asn Ser Asn Ile Asp Thr Pro Ile
530                 535                 540 tct gct ctt cct agt cgg ttc gtc tcg gat gcg ctt ctc ccg tca ccg    1680
Ser Ala Leu Pro Ser Arg Phe Val Ser Asp Ala Leu Leu Pro Ser Pro
545                 550                 555                 560 tcc agt ttc ttt ccg gaa tgg ggc ttt ggg cgg tct gga cca gac agc    1728
Ser Ser Phe Phe Pro Glu Trp Gly Phe Gly Arg Ser Gly Pro Asp Ser
                565                 570                 575 aac atg ttg ccc agt ccc ttg acg ttc cct acg ccg gcg gta caa agt    1776
Asn Met Leu Pro Ser Pro Leu Thr Phe Pro Thr Pro Ala Val Gln Ser
            580                 585                 590 ggc ccc ggg ttt ggg cgc gag gat gag caa gac aaa aag cgc aaa agc    1824
Gly Pro Gly Phe Gly Arg Glu Asp Glu Gln Asp Lys Lys Arg Lys Ser
            595                 600                 605 cct gat agt gga ccc aat gcg gaa ggg gta gtg aag aaa cca aag acg    1872
Pro Asp Ser Gly Pro Asn Ala Glu Gly Val Val Lys Lys Pro Lys Thr
610                 615                 620
``` taa                                                                    1875

<210> SEQ ID NO 3
<211> LENGTH: 624
<212> TYPE: PRT
<213> ORGANISM: Aspergillus niger

<400> SEQUENCE: 3

Met Gly Arg Arg Lys Ile Glu Ile Lys Ala Ile Lys Asp Asp Arg Asn
1               5                   10                  15

Arg Ser Val Thr Phe Leu Lys Arg Lys Gly Gly Leu Phe Lys Lys Ala
            20                  25                  30

His Glu Leu Ala Val Leu Cys Ser Val Asp Val Ala Val Ile Ile Phe
        35                  40                  45

Gly His Asn Lys Lys Leu Tyr Glu Phe Ser Ser Cys Asp Met Arg Glu
    50                  55                  60

Ala Leu Thr Arg Tyr Gln Tyr Phe Gly Pro Pro His Glu His Lys Gly
65                  70                  75                  80

Pro Glu Asp Phe Asn Gly Lys Arg Asp Asp Asp Asp Glu Asp Glu
                85                  90                  95

Thr Thr Pro Ala Pro Glu Asp Val His Pro Thr Pro Asn Pro Pro
            100                 105                 110

Met Ile Pro Ala His Leu Pro Gly His Pro Gly Phe Gln His Val Thr
        115                 120                 125

His Ala Pro Ser Ala Ser Pro Pro Ile Gly Asn Gly Met Ala Phe Ala
    130                 135                 140

Pro Arg His Gly Thr Pro Gln Pro Gln Gly Val Ser Arg Pro Ser Ser
145                 150                 155                 160

Arg Asn His Leu Arg Arg Val Ser Ser Asn Met Gly Pro Gln Gln His
                165                 170                 175

His His Ala Thr Pro Pro Pro Pro Pro Pro Gln Asn Gly Phe
            180                 185                 190

Thr Tyr Ile Pro Asn Pro Ser Val Tyr Asn Pro Asn Ala Ala His Ala
        195                 200                 205

Met Ala Gln Pro Pro Arg Pro Pro Gln Phe Thr His Tyr Gly Pro Pro
    210                 215                 220

Gly Pro His His Gln Pro Pro Pro Gln His His Pro Ala Met
225                 230                 235                 240

Pro Pro His Ser Met Pro Pro Gln Ser Met Pro Pro His Thr Met Ala
                245                 250                 255

Pro Gln Ala Met Pro Pro His His Gln Ala Pro Pro His Met Pro His
            260                 265                 270

Pro Pro His Ala Leu Ser Gln Gln Pro Pro Pro Met Ala Met Thr Gln
        275                 280                 285

Pro Pro His Ala Ala Ile Pro Gln Val Ala Gln Ala Phe Leu Pro Glu
    290                 295                 300

Gln Gly Arg Asn Ser Met Pro Pro Thr Phe Thr Glu Gln Gln Pro
305                 310                 315                 320

Pro Pro Pro Arg Thr Val Ser Leu Pro Glu Gly Thr Ala Pro Thr Asp
                325                 330                 335

Ala Met Pro Gly Pro Met Lys Thr Glu Gly Thr Pro Ser Pro Pro His
            340                 345                 350

Gln Arg Ser Leu Ser Ser Lys Ser Arg Ser Ile Phe Thr Pro Ile Asp
        355                 360                 365

Asp Arg Gly Ser Val Leu Ala Arg His Phe Gly Val Gly Pro Pro Thr
370                 375                 380

Glu Ala Gly Glu Asn Ala Gln Thr Lys Ala Glu Gly Ala Thr Leu Gly
385                 390                 395                 400

Pro Asn Glu Gly Lys Pro Ala Gly Leu Thr Ala Lys Pro Pro Pro
            405                 410                 415

Pro Pro Arg Ala Ala Thr Glu Ala Pro Arg Pro Gln Pro Val Val Asp
            420                 425                 430

Leu Lys Pro Pro Val Arg Thr Asn Ser Gly Gln Phe Pro Pro Lys Arg
            435                 440                 445

Pro Gln Leu Lys Val Gln Ile Pro Ser Glu Asn Ser Asp Arg Gly Ser
450                 455                 460

Ala Thr Ala Asp Ser Ser Arg Asp Ser Ala Gly Asn Lys Thr Leu
465                 470                 475                 480

Thr Pro Ala Lys Ala Asn Pro Asp Thr Gly His Ser Ser Val Val Leu
            485                 490                 495

Pro Pro Pro Ser Pro Ser Ala Gly Ala Ile Leu Ser Ala Gly Ala Gln
            500                 505                 510

Gly Pro Pro Asn Pro Phe Ala Arg Pro Pro Pro Gly Ala Ala Pro
            515                 520                 525

Gln Asn Asn Ser Ala Tyr Asn Asn Ser Asn Ile Asp Thr Pro Ile
530                 535                 540

Ser Ala Leu Pro Ser Arg Phe Val Ser Asp Ala Leu Leu Pro Ser Pro
545                 550                 555                 560

Ser Ser Phe Phe Pro Glu Trp Gly Phe Gly Arg Ser Gly Pro Asp Ser
            565                 570                 575

Asn Met Leu Pro Ser Pro Leu Thr Phe Pro Thr Pro Ala Val Gln Ser
            580                 585                 590

Gly Pro Gly Phe Gly Arg Glu Asp Glu Gln Asp Lys Lys Arg Lys Ser
            595                 600                 605

Pro Asp Ser Gly Pro Asn Ala Glu Gly Val Val Lys Lys Pro Lys Thr
610                 615                 620

<210> SEQ ID NO 4
<211> LENGTH: 37
<212> TYPE: DNA
<213> ORGANISM: Artificial sequence
<220> FEATURE:
<223> OTHER INFORMATION: Primer HTJP-520

<400> SEQUENCE: 4
accgcggtgg cggccgcatt gggaaacata ccgcctc         37

<210> SEQ ID NO 5
<211> LENGTH: 36
<212> TYPE: DNA
<213> ORGANISM: Artificial sequence
<220> FEATURE:
<223> OTHER INFORMATION: Primer HTJP-521

<400> SEQUENCE: 5
ggttcgctcc actagttttc cgggacgcga ttagag          36

<210> SEQ ID NO 6
<211> LENGTH: 45
<212> TYPE: DNA
<213> ORGANISM: Artificial sequence
<220> FEATURE:
<223> OTHER INFORMATION: Primer HTJP-523

-continued

<400> SEQUENCE: 6
gcctacagga gaattcttaa ttaaacgaac tagatctttc acctg           45

<210> SEQ ID NO 7
<211> LENGTH: 35
<212> TYPE: DNA
<213> ORGANISM: Artificial sequence
<220> FEATURE:
<223> OTHER INFORMATION: Primer HTJP-525

<400> SEQUENCE: 7
ctcgtaagct tctagaattg acgaccgagg ctccg                      35

<210> SEQ ID NO 8
<211> LENGTH: 20
<212> TYPE: DNA
<213> ORGANISM: Artificial sequence
<220> FEATURE:
<223> OTHER INFORMATION: Primer HTJP-553

<400> SEQUENCE: 8
gctaaaggtg atggaactgc                                       20

<210> SEQ ID NO 9
<211> LENGTH: 20
<212> TYPE: DNA
<213> ORGANISM: Artificial sequence
<220> FEATURE:
<223> OTHER INFORMATION: Primer HTJP-554

<400> SEQUENCE: 9
gagtgacggt attttggagg                                       20

<210> SEQ ID NO 10
<211> LENGTH: 2099
<212> TYPE: DNA
<213> ORGANISM: Artificial sequence
<220> FEATURE:
<223> OTHER INFORMATION: Synthetic codon-optimized Kionochaeta sp.
      PLC-encoding sequence

<400> SEQUENCE: 10
atgagggcct cctccatctt gagcttagcg ttgggtttgt ccgttgctca ggccgcggtc    60
aaccctgctg acgtcttatc cgtggtcgaa aagagggttg atcctgctag tgggctcgaa   120
gtcaggtcga tttgggatac tatttggaac gatatcaaat ctgctgccga ctgtacggca   180
tgtgaggtct gtctctccac ttgacacttt ggtagtagcg ctcgatgctc acccttcata   240
catctccata ggctgtcctt accttgttaa aaggtgtcgc agcctttggt gacaacttct   300
ttgtggaagt gctgacggaa atttgcgatc tgagtgggta tgcttttgag ttcatagctc   360
tgttgaccag gctgaaagtt tcccagggc cgaggacgac gacgtctgtt cgggtgtgct   420
ctccctggaa ggtccaatca ttgccaacga cattcgcaag atgtctattg ggtcgaagac   480
gtctgaactc ttttgtatca ccttcttggg cctgtgctcg tatccagcag tggatgcgtt   540
taccgtgccg tttccaactg ccaaatcggc ggccactcgt ccggtttcga gcggaaaaga   600
tcctatctat gtcgtccact atagtgacat ccacatagat ccattttacg tcgccggctc   660
agcgtatgcg atcttcaccc agataccagc ggacagtagc tgaccatttt tccagttcga   720
attgcaccaa gcccatctgc tgccgtgatt atacttccgc gagcagtcca ggtaataaca   780
actcgccggc aggaccgtat ggcgatcaca actgcgatgt gcccatcagc ctggaagaca   840

-continued

```
gcatgtacgc agctatcaaa aagctcgtcc ccgatgccgc gttcggtata ttcacaggcg      900
atatcgttga tcacgccgtc tggaatacct ccgaatccca gaacattatc gacatgaacg      960
acgcctacac ccgcatgaaa aacagcggga tgcttccgac gatcttcgca accgcaggta     1020
accacgaggc ttctccagtg aactccttcc cgccacccgc catcggtaac gagagccagt     1080
gggtttacga caccctcgca tctgactgga gccaatggat cggaacctcc ggtgccagca     1140
gcgtggagtc tattggcgcc tattcagtcc agtacggctc cacaaagctg cgcgttatct     1200
ccttgaacac caacatgtac tacatcgaga atttctacct ctacgagcca accatggaac     1260
aggaccctgc gggccagttc gcctggctcg tgtcggagct ctctgcagcc gaggcagccg     1320
gcgaacgcgt ctggatcatt ggccacatgc cctgggact agcgacgcc ttccacgacc       1380 cctctaacta cttcgatcag atcgtcaacc gctacgaggc caccatcgcc gccatgttct     1440
ttggccacac tcacgaggac cactttcaga tctcctactc cgactacaac gcgcgtacgg     1500
cagctaacgc acgggcagtc tcctacatca tgccctcatt gaccccgacc tctggtcacc     1560
ctactttccg cgtctacact gtcgaccccg agactttcgg agtcctcgat gccaccactt     1620
actacgctga catgtcccag ccgacctatc agacagccgg cccagcttgg tccgtttact     1680
actccgctaa ggcggcgtac ggaggactgg tcgacccgcc cgttgccgcc gacgacgccg     1740
ccgctgaatt gaccccctgct ttctggcaca atgtcactgc cgcgcttgct gctgatcctg     1800
cctcgttcga cgcctattat gcccgcaaga cccgaggctg ggatgtcgct gcctgtgcag     1860
gtgcctgtgc tgccgccgag gtttgcgctt tgcgtgctgc tcgtgcacag gataattgtg     1920
tggttcccac ccctggggtt cacttcagca agcgcgctga cgagggtacc cttgcccacc     1980
accgtgacga gtgtggtgtc tcggtggccc gcaatagtct gtcgtctctt gtcgtccagc     2040
gcgaagccct cgagcacctc gagggacgac tcagcgagaa acgccggatg gccgtttag    2099
```

<210> SEQ ID NO 11
<211> LENGTH: 39
<212> TYPE: DNA
<213> ORGANISM: Artificial sequence
<220> FEATURE:
<223> OTHER INFORMATION: Primer

<400> SEQUENCE: 11

```
agtcttgatc ggatccacca tgagggcctc ctccatctt                              39
```

<210> SEQ ID NO 12
<211> LENGTH: 43
<212> TYPE: DNA
<213> ORGANISM: Artificial sequence
<220> FEATURE:
<223> OTHER INFORMATION: Primer

<400> SEQUENCE: 12

```
cgttatcgta cgcaccacgt gctaaacggc catccggcgt ttc                         43
```

<210> SEQ ID NO 13
<211> LENGTH: 20
<212> TYPE: DNA
<213> ORGANISM: Artificial sequence
<220> FEATURE:
<223> OTHER INFORMATION: Primer IH198

<400> SEQUENCE: 13

```
gtcactgccg cgcttgctgc                                                   20
```

```
<210> SEQ ID NO 14
<211> LENGTH: 31
<212> TYPE: DNA
<213> ORGANISM: artificial sequence
<220> FEATURE:
<223> OTHER INFORMATION: Primer HTJP-375

<400> SEQUENCE: 14
ccgcacgtgc taaacggcca tccggcgttt c                              31
```

RLMA-INACTIVATED FILAMENTOUS FUNGAL HOST CELL

CROSS-REFERENCE TO RELATED APPLICATIONS

This application is a 35 U.S.C. § 371 national application of PCT/EP2017/059129 filed Apr. 18, 2017, which claims priority or the benefit under 35 U.S.C. § 119 of European Application No. 16176897.3 filed Jun. 29, 2016, and European Application No. 16165997.4 filed Apr. 19, 2016, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to modified filamentous fungal cells and to methods for producing such cells as well as methods of producing secreted polypeptides of interest therein.

BACKGROUND OF THE INVENTION

It has been shown that the rlmA gene in *Aspergillus niger* is a so-called MADS-box transcription factor and that it is required for resistence toward cell wall stresses. An *A. niger* rlmA deletion mutant was shown to be more sensitive to cell wall stresses such as heat stress and cell wall synthesis inhibitors (e.g. chitin syhthesis inhibitor; Calcoflour white). RImA has also been shown to regulate the agsA gene in *A. niger*, an intracellular β-glucuronidase (GUS) reporter encoded by the uidA gene was operably linked with several version of the agsA promoter and the expression was assayed (Damveld R A et al, Mol Microbiol 2005, 58:305-19; Fiedler et al. Fungal Biology and Biotechnology 2014, 1:5).

SUMMARY OF THE INVENTION

The present invention is directed to genetically modified filamentous fungal host cells in which the rlmA gene has been inactivated. Inactivation of the rlmA gene may be done by any suitable gene inactivation method known in the art. An example of a convenient way to eliminate or reduce rlmA expression is based on techniques of gene replacement or gene interruption.

The inactivation of rlmA in an *Aspergillus* filamentous fungal host cell resulted in increased yield of a heterologous secreted polypeptide of interest expressed in the cell.

Accordingly, in a first aspect, the invention relates to filamentous fungal host cells comprising a heterologous polynucleotide encoding a secreted polypeptide of interest and comprising an inactivated rlmA gene or homologue thereof, wherein said rlmA gene or homologue thereof encodes an RImA polypeptide having at least 80% amino acid sequence identity with SEQ ID NO:3.

The invention further provides methods for producing a heterologous secreted polypeptide of interest by cultivating a filamentous fungal host cell of the invention under conditions conducive for expression of the polypeptide of interest and, optionally, recovering the polypeptide of interest.

Accordingly, in a second aspect, the invention relates to methods of producing a secreted polypeptide of interest, said method comprising the steps of:
a) cultivating a filamentous fungal host cell comprising a heterologous polynucleotide encoding the secreted polypeptide of interest and comprising an inactivated rlmA gene or homologue thereof under conditions conducive to the expression of the secreted polypeptide of interest, wherein said rlmA gene or homologue thereof encodes an RImA polypeptide having at least 80% amino acid sequence identity with SEQ ID NO:3; and, optionally,
b) recovering the secreted polypeptide of interest.

In a final aspect, the invention relates to methods of producing a filamentous fungal host cell having an improved yield of a secreted heterologous polypeptide of interest, said method comprising the following steps in no particular order:
a) transforming a filamentous fungal host cell with a heterologous polynucleotide encoding the secreted polypeptide of interest; and
b) inactivating an rlmA gene or a homologue thereof in the filamentous fungal host cell, wherein said rlmA gene or a homologue thereof encodes an RImA polypeptide having at least 80% amino acid sequence identity with SEQ ID NO:3.

Definitions cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

DETAILED DESCRIPTION OF THE INVENTION

Host Cells

The present invention relates to recombinant host cells comprising a polynucleotide of the present invention operably linked to one or more control sequences that direct the production and secretion of a heterologous polypeptide of interest.

A construct or vector comprising a polynucleotide is introduced into a host cell so that the construct or vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell of the invention is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic.

The filamentous fungal host cell may be an *Acremonium, Aspergillus, Aureobasidium, Bjerkandera, Ceriporiopsis, Chtysosporium, Coprinus, Coriolus, Cryptococcus, Filibasidium, Fusarium, Humicola, Magnaporthe, Mucor, Myceliophthora, Neocaffimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans,*

*Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chtysosporium inops, Chtysosporium keratinophilum, Chtysosporium lucknowense, Chrysosporium merdarium, Chtysosporium pannicola, Chtysosporium queenslandicum, Chtysosporium tropicum, Chtysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulaturn, Fusarium roseum, Fusarium sambucinum, Fusarium sarcochroum, Fusarium sporotrichioides, Fusarium sulphureum, Fusarium torulosum, Fusarium trichothecioides, Fusarium venenatutn, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, Gene 78: 147-156, and WO 96/00787.

In one aspect, the invention relates to methods of producing a filamentous fungal host cell having an improved yield of a secreted heterologous polypeptide of interest, said method comprising the following steps in no particular order:
c) transforming a filamentous fungal host cell with a heterologous polynucleotide encoding the secreted polypeptide of interest; and
d) inactivating an rlmA gene or a homologue thereof in the filamentous fungal host cell, wherein said rlmA gene or a homologue thereof encodes an RImA polypeptide having at least 80% amino acid sequence identity with SEQ ID NO:3.

In another aspect, the invention relates to the resulting host cells; filamentous fungal host cells comprising a heterologous polynucleotide encoding a secreted polypeptide of interest and comprising an inactivated rlmA gene or homologue thereof, wherein said rlmA gene or homologue thereof encodes an RImA polypeptide having at least 80% amino acid sequence identity with SEQ ID NO:3.

In a preferred embodiment of the aspects of the invention, the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*; even more preferably the filamentous fungal host cell is an *Aspergillus* cell; preferably an *Aspergillus awamori, Aspergillus foetidus, Aspergillus fumigatus, Aspergillus japonicus, Aspergillus nidulans, Aspergillus niger* or an *Aspergillus oryzae* cell.

Preferably, the secreted polypeptide of interest is an enzyme; preferably the enzyme is a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, xylanase, or beta-xylosidase.

In a preferred embodiment of the invention, the RImA polypeptide comprises or consists of an amino acid sequence at least 80% identical to the amino acid sequence shown in SEQ ID NO:3; preferably at least 85%, 90%, 95%, 96%, 97%, 98% or most preferably at least 99% identical to the amino acid sequence shown in SEQ ID NO:3.

Preferably, the rlmA gene or homologue thereof comprises or consists of a genomic nucleotide sequence at least 80% identical to the genomic DNA sequence shown in SEQ ID NO:1; preferably at least 85%, 90%, 95%, 96%, 97%, 98% or most preferably at least 99% identical to the genomic DNA sequence shown in SEQ ID NO:1. Alternatively, the rlmA gene or homologue thereof comprises or consists of a genomic nucleotide sequence, the cDNA sequence of which is at least 80% identical to the cDNA sequence shown in SEQ ID NO:2; preferably at least 85%, 90%, 95%, 96%, 97%, 98% or most preferably at least 99% identical to the cDNA sequence shown in SEQ ID NO:2.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5′-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANS1 (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Removal or Reduction of RlmA Activity

The present invention also relates to methods of producing a mutant of a parent cell, which comprises inactivating, disrupting or deleting a polynucleotide, or a portion thereof, encoding an RlmA polypeptide of the present invention, which results in the mutant cell producing less of the RlmA polypeptide than the parent cell when cultivated under the same conditions.

The mutant cell may be constructed by reducing or eliminating expression of the rlmA polynucleotide or a homologue thereof using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the rImA polynucleotide or homologue thereof may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

Methods for deleting or disrupting a targeted gene are described, for example, by Miller, et al (1985. Mol. Cell. Biol. 5:1714-1721); WO 90/00192; May, G. (1992. Applied Molecular Genetics of Filamentous Fungi. J. R. Kinghorn and G. Turner, eds., Blackie Academic and Professional, pp. 1-25); and Turner, G. (1994. Vectors for Genetic Manipulation. S. D. Martinelli and J. R. Kinghorn, eds., Elsevier, pp. 641-665).

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having RImA activity in a cell, comprising administering to the cell or expressing in the cell a double-stranded RNA (dsRNA) molecule, wherein the dsRNA comprises a subsequence of an rImA polynucleotide or homologue thereof. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi); see, for example, U.S. Pat. No. 5,190,931.

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824 and 6,515,109.

The RImA polypeptide-deficient mutant cells are particularly useful as host cells for expression of heterologous secreted polypeptides.

The methods used for cultivation and purification of the product of interest may be performed by methods known in the art.

Methods of Production

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

One aspect of the invention relates to methods of producing a secreted polypeptide of interest, said method comprising the steps of:
- a) cultivating a filamentous fungal host cell comprising a heterologous polynucleotide encoding the secreted polypeptide of interest and comprising an inactivated rlmA gene or homologue thereof under conditions conducive to the expression of the secreted polypeptide of interest, wherein said rlmA gene or homologue thereof encodes an RlmA polypeptide having at least 80% amino acid sequence identity with SEQ ID NO:3; and, optionally,
- b) recovering the secreted polypeptide of interest.

In a preferred embodiment, the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*; even more preferably the filamentous fungal host cell is an *Aspergillus* cell; preferably an *Aspergillus awamori, Aspergillus foetidus, Aspergillus fumigatus, Aspergillus japonicus, Aspergillus nidulans, Aspergillus niger* or an *Aspergillus oryzae* cell.

Preferably, the secreted polypeptide of interest is an enzyme; preferably the enzyme is a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

In a preferred embodiment of the invention, the RlmA polypeptide comprises or consists of an amino acid sequence at least 80% identical to the amino acid sequence shown in SEQ ID NO:3; preferably at least 85%, 90%, 95%, 96%, 97%, 98% or most preferably at least 99% identical to the amino acid sequence shown in SEQ ID NO:3.

Preferably, the rlmA gene or homologue thereof comprises or consists of a genomic nucleotide sequence at least 80% identical to the genomic DNA sequence shown in SEQ ID NO:1; preferably at least 85%, 90%, 95%, 96%, 97%, 98% or most preferably at least 99% identical to the genomic DNA sequence shown in SEQ ID NO:1. Alternatively, the rlmA gene or homologue thereof comprises or consists of a genomic nucleotide sequence, the cDNA sequence of which is at least 80% identical to the cDNA sequence shown in SEQ ID NO:2; preferably at least 85%, 90%, 95%, 96%, 97%, 98% or most preferably at least 99% identical to the cDNA sequence shown in SEQ ID NO:2.

EXAMPLES

Materials and Methods

Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology", John Wiley and Sons, 1995; Harwood, C. R., and Cutting, S. M. (eds.) "Molecular Biological Methods for Bacillus". John Wiley and Sons, 1990.

Purchased Material (*E. coli* and Kits)

*E. coli* DH5α (Toyobo) is used for plasmid construction and amplification. Amplified plasmids are recovered with Qiagen Plasmid Kit (Qiagen). Ligation is done with DNA ligation kit (Takara) or T4 DNA ligase (Boehringer Mannheim). Polymerase Chain Reaction (PCR) is carried out with Expand™ PCR system (Boehringer Mannheim). QIAquick™ Gel Extraction Kit (Qiagen) is used for the purification of PCR fragments and extraction of DNA fragment from agarose gel.

Enzymes

Enzymes for DNA manipulations (e.g. restriction endonucleases, ligases etc.) are obtainable from New England Biolabs, Inc. and were used according to the manufacturer's instructions.

Plasmids pBluescript II SK- (Stratagene #212206).

The pHUda801 harbouring *A. nidulans* pyrG gene and herpes simplex virus (HSV) thymidine kinase gene (TK) driven by *A. nidulans* glyceraldehyde-3-phosphate dehydrogenase promoter (Pgpd) and *A. nidulans* tryptophane synthase terminator (TtrpC) are described in example 4 in WO2012/160093.

The sequence information for Gs AMG harboring the amyloglucosidase from Gloeophyllum sepiarium is disclosed in Example 1 (SEQ ID NO:2) in WO2011/068803.

Microbial Strains

The expression host strain *Aspergillus niger* M1412 (pyrG-phenotype/uridine auxotrophy) was isolated by Novozymes and is a derivative of *Aspergillus niger*NN049184 which was isolated from soil described in example 14 in WO2012/160093. M1412 is a strain which can produce the glucoamylase (1,4-alpha-D-glucan glucohydrolase, EC 3.2.1.3) from Gloeophyllum sepiarium (Gs AMG).

Medium

COVE trace metals solution was composed of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

50×COVE salts solution was composed of 26 g of KCl, 26 g of $MgSO_4.7H_2O$, 76 g of $KH_2PO_4$, 50 ml of COVE trace metals solution, and deionized water to 1 liter.

COVE medium was composed of 342.3 g of sucrose, 20 ml of 50×COVE salts solution, 10 ml of 1 M acetamide, 10 ml of 1.5 M CsCl2, 25 g of Noble agar, and deionized water to 1 liter.

COVE-N-Gly plates were composed of 218 g of sorbitol, 10 g of glycerol, 2.02 g of KNO3, 50 ml of COVE salts solution, 25 g of Noble agar, and deionized water to 1 liter.

COVE-N (tf) was composed of 342.3 g of sucrose, 3 g of NaNO3, 20 ml of COVE salts solution, 30 g of Noble agar, and deionized water to 1 liter.

COVE-N top agarose was composed of 342.3 g of sucrose, 3 g of NaNO3, 20 ml of COVE salts solution, 10 g of low melt agarose, and deionized water to 1 liter.

COVE-N was composed of 30 g of sucrose, 3 g of NaNO3, 20 ml of COVE salts solution, 30 g of Noble agar, and deionized water to 1 liter.

STC buffer was composed of 0.8 M sorbitol, 25 mM Tris pH 8, and 25 mM CaCl$_2$).

STPC buffer was composed of 40% PEG 4000 in STC buffer.

LB medium was composed of 10 g of tryptone, 5 g of yeast extract, 5 g of sodium chloride, and deionized water to 1 liter.

LB plus ampicillin plates were composed of 10 g of tryptone, 5 g of yeast extract, 5 g of sodium chloride, 15 g of Bacto agar, ampicillin at 100 µg per ml, and deionized water to 1 liter.

YPG medium was composed of 10 g of yeast extract, 20 g of Bacto peptone, 20 g of glucose, and deionized water to 1 liter.

SOC medium was composed of 20 g of tryptone, 5 g of yeast extract, 0.5 g of NaCl, 10 ml of 250 mM KCl, and deionized water to 1 liter.

TAE buffer was composed of 4.84 g of Tris Base, 1.14 ml of Glacial acetic acid, 2 ml of 0.5 M EDTA pH 8.0, and deionized water to 1 liter.

Transformation of *Aspergillus*

Transformation of *Aspergillus* species can be achieved using the general methods for yeast transformation. The preferred procedure for the invention is described below.

*Aspergillus niger* host strain was inoculated to 100 ml of YPG medium supplemented with 10 mM uridine and incubated for 16 hrs at 32° C. at 80 rpm. Pellets were collected and washed with 0.6 M KCl, and resuspended 20 ml 0.6 M KCl containing a commercial β-glucanase product (GLU-CANEX™, Novozymes NS, Bagsvrd, Denmark) at a final concentration of 20 mg per ml. The suspension was incubated at 32° C. at 80 rpm until protoplasts were formed, and then washed twice with STC buffer.

The protoplasts were counted with a hematometer and resuspended and adjusted in an 8:2:0.1 solution of STC: STPC:DMSO to a final concentration of 2.5×10$^7$ protoplasts/ml. Approximately 4 µg of plasmid DNA was added to 100 µl of the protoplast suspension, mixed gently, and incubated on ice for 30 minutes. One ml of SPTC was added and the protoplast suspension was incubated for 20 minutes at 37° C. After the addition of 10 ml of 50° C. Cove or Cove-N top agarose, the reaction was poured onto Cove or Cove-N (if) agar plates and the plates were incubated at 32° C. for 5 days.

PCR Amplifications in Example 1

| Component | Volume | Final Concentration |
| --- | --- | --- |
| 10x Buffer for KOD -Plus- | 5 µl | 1x |
| 2 mM dNTPs | 5 µl | 0.2 mM each |
| 25 mM MgSO$_4$ | 2 µl | 1.0 mM |
| 10 pmol/µl Primer #1 | 1.5 µl | 0.3 µM |
| 10 pmol/µl Primer #2 | 1.5 µl | 0.3 µM |
| Template DNA | X µl | |
| Genomic DNA Plasmid DNA | 10-200 ng/50 µl | |
| | 1-50 ng/50 µl | |
| PCR grade water | Y µl | |
| KOD-Plus- (1.0 U/µl) | 1 µl | 1.0 U/50 µl |
| Total reaction volume | 50 µl | |

3-Step Cycle:

Pre-denaturation: 94° C., 2 min.

Denaturation: 94° C., 15 sec. ⎫
Annealing Tm-[5-10]° C.*, 30 sec. ⎬ 35 cycles
Extension: 68° C., 1 min./kb ⎭

Lab-Scale Tank Cultivation for Gs AMG Production

Fermentation was done as fed-batch fermentation (H. Pedersen 2000, Appl Microbiol Biotechnol, 53: 272-277). Selected strains were pre-cultured in liquid media then grown mycelia were transferred to the tanks for further cultivation of enzyme production. Cultivation was done at pH 4.75 at 34° C. for 7 days with the feeding of glucose and ammonium without over-dosing which prevents enzyme production. Culture supernatant after centrifugation was used for enzyme assay.

Sequences

SEQ ID NO: 1:
*Aspergillus niger* rlmA genomic DNA sequence

SEQ ID NO: 2:
*Aspergillus niger* rlmA coding sequence

SEQ ID NO: 3:
*Aspergillus niger* rlmA amino acid sequence

SEQ ID NO: 4:
Primer HTJP-520
5' accgcggtggcggccgcattgggaaacataccgcctc

SEQ ID NO: 5:
Primer HTJP-521
5' ggttcgctccactagttttccgggacgcgattagag

SEQ ID NO: 6:
Primer HTJP-523
5' gcctacaggagaattcttaattaaacgaactagatctttcacctg

SEQ ID NO: 7:
Primer HTJP-525
5' ctcgtaagcttctagaattgacgaccgaggctccg

SEQ ID NO: 8:
Primer HTJP-553
5' gctaaaggtgatggaactgc

SEQ ID NO: 9:
Primer HTJP-554
5' gagtgacggtattttggagg

Glucoamylase Activity

Glucoamylase activity is measured in AmyloGlucosidase Units (AGU). The AGU is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes. An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

Amyloglycosidase Incubation:

| | |
| --- | --- |
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

Color Reaction:

| | |
| --- | --- |
| GlucDH: | 430 U/L |
| Mutarotase: | 9 U/L |

-continued

| NAD: | 0.21 mM |
| --- | --- |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Example 1 Disruption of the rlmA Gene in *Aspergillus niger*

Construction of the rlmA Gene Disruption Plasmid pHiTe177

Plasmid pHiTe177 was constructed to contain 5' and 3' flanking regions for the *Aspergillus niger* rlmA gene separated by the *A. nidulans* orotidine-5'-phosphate decarboxylase gene (pyrG) as a selectable marker with its terminator repeats, and the human Herpes simplex virus 1 (HSV-1) thymidine kinase gene. The HSV-1 thymidine kinase gene lies 3' of the 3' flanking region of the rlmA gene, allowing for counter-selection of *Aspergillus niger* transformants that do not correctly target to the rlmA gene locus. The plasmid was constructed in several steps as described below.

A PCR product containing the 5' flanking region of *A. niger* rlmA was generated using the following primers:

```
SEQ ID NO: 4:
Primer HTJP-520:
5' accgcggtggcggccgcattgggaaacataccgcctc

SEQ ID NO: 5:
Primer HTJP-521:
5' ggttcgctccactagttttccgggacgcgattagag
```

The desired fragment was amplified by PCR in a reaction composed of approximately 100 ng of genome DNA of *Aspergillus niger* M1412 as described in material and method. The reaction was incubated in a Bio-Rad® C1000 Touch™ Thermal Cycler programmed for 1 cycle at 94° C. for 2 minutes; 35 cycles each at 94° C. for 15 seconds, 55° C. for 30 seconds, and 68° C. for 2 minutes; and a 4° C. hold. The resulting 1,495 bp PCR fragment was purified by 0.8% agarose gel electrophoresis using TAE buffer, excised from the gel, and extracted using a QIAQUICK® Gel Extraction Kit.

Plasmid pHUda801 (Example 4 in WO 2012160093 A1) was digested with NotI-HF and SpeI-HF (New England Biolabs Inc.), and purified by 0.8% agarose gel electrophoresis using TAE buffer, where a 9,558 bp fragment was excised from the gel and extracted using a QIAQUICK® Gel Extraction Kit. The 9,558 bp fragment was ligated to the 1,495 bp PCR fragment by using the In-Fusion kit (Clontech Laboratories, Inc.) according to the manufactory instructions. The reaction was performed at 50° C. for 15 minutes. 1 µl of the reaction mixture were transformed into DH5a chemically competent *E. coli* cells. Transformants were spread onto LB plus ampicillin plates and incubated at 37° C. overnight. Plasmid DNA was purified from several transformants using a QIA mini-prep kit. The plasmid DNA was screened for proper ligation by use of proper restriction enzymes followed by 0.8% agarose gel electrophoresis using TAE buffer. One plasmid was designated as pHiTe177-5'rlmA A PCR product containing the 3' flanking region of *A. niger* rlmA was generated using the following primers:

```
SEQ ID NO: 6:
Primer HTJP-523:
5' gcctacaggagaattcttaattaaacgaactagatctttcacctg SEQ ID NO: 7:
Primer HTJP-555:
5' ctcgtaagcttctagaattgacgaccgaggctccg
```

The desired fragment was amplified by PCR in a reaction composed of approximately 100 ng of genome DNA of *Aspergillus niger* M1412 as described in material and method. The reaction was incubated in a Bio-Rad® C1000 Touch™ Thermal Cycler programmed for 1 cycle at 94° C. for 2 minutes; 35 cycles each at 94° C. for 15 seconds, 55° C. for 30 seconds, and 68° C. for 2 minutes; and a 4° C. hold. The 1,915 bp PCR fragment was purified by 0.8% agarose gel electrophoresis using TAE buffer, excised from the gel, and extracted using a QIAQUICK® Gel Extraction Kit.

Plasmid pHiTe177-5'rlmA was digested with XbaI and EcoRI-HF (New England Biolabs Inc.), and purified by 0.8% agarose gel electrophoresis using TAE buffer, where a 8,997 bp fragment was excised from the gel and extracted using a QIAQUICK® Gel Extraction Kit. The 8,997 bp fragment was ligated to the 1,915 bp PCR fragment by using the In-Fusion kit (Clontech Laboratories, Inc.) according to the manufactory instructions. The reaction was performed at 50° C. for 10 minutes. Five µl of the ligation mixture were transformed into DH5a chemically competent *E. coli* cells. Transformants were spread onto LB plus ampicillin plates and incubated at 37° C. overnight. Plasmid DNA was purified from several transformants using a QIA mini-prep kit. The plasmid DNA was screened for proper ligation by use of proper restriction enzymes followed by 0.8% agarose gel electrophoresis using TAE buffer. One plasmid was designated as pHiTe177.

The rlmA-Disruption in *Aspergillus niger* Strain M1412

Protoplasts of *Aspergillus niger* strain M1412 were prepared by cultivating the strain in 100 ml of YPG medium supplemented with 10 mM uridine at 32° C. for 16 hours with gentle agitation at 80 rpm. Pellets were collected and washed with 0.6 M KCl, and resuspended 20 ml 0.6 M KCl containing a commercial β-glucanase product (GLU-CANEX™, Novozymes A/S, Bagsvrd, Denmark) at a final concentration of 20 mg per ml. The suspension was incubated at 32° C. at 80 rpm until protoplasts were formed. Protoplasts were filtered through a funnel lined with MIRA-CLOTH® into a 50 ml sterile plastic centrifuge tube and were washed with 0.6 M KCl to extract trapped protoplasts. The combined filtrate and supernatant were collected by centrifugation at 2,000 rpm for 15 minutes. The supernatant was discarded and the pellet was washed with 10-25 ml of STC and centrifuged again at 2,000 rpm for 10 minutes and then washed twice with STC buffer. The protoplasts were counted with a hematometer and resuspended and adjusted in an 8:2:0.1 solution of STC:STPC:DMSO to a final concentration of $2.5 \times 10^7$ protoplasts/ml.

Approximately 10 µg of pHiTe177 was added to 0.4 ml of the protoplast suspension, mixed gently, and incubated on ice for 30 minutes. Three ml of SPTC was added and the protoplast suspension was incubated for 20 minutes at 37° C. After the addition of 12 ml of 50° C. COVE-N top agarose, the mixture was poured onto the COVE-N plates and the plates were incubated at 30° C. for 7 days. The grown transformants were transferred with sterile toothpicks to Cove-N JP plates supplemented with 1.5 µM 5-Flouro-2-deoxyuridine (FdU), an agent which kills cells expressing the herpes simplex virus (HSV) thymidine kinase gene (TK) harboring in pHiTe177. Single spore isolates were transferred to COVE-N-gly plates.

Possible transformants of *Aspergillus niger* strain M1412 containing the pHiTe177 to disrupt rlmA gene were screened by Southern blot analysis. Each of the spore purified transformants were cultivated in 3 ml of YPG medium and incubated at 30° C. for 2 days with shaking at 200 rpm. Biomass was collected using a MIRACLOTH® lined funnel. Ground mycelia were subject to genome DNA preparation using FastDNA SPIN Kit for Soil (MP Biomedicals) follows by manufacture's instruction.

Southern blot analysis was performed to confirm the disruption of the rlmA gene locus. Five µg of genomic DNA from each transformant were digested with NcoI-HF. The genomic DNA digestion reactions were composed of 5 µg of genomic DNA, 1 µl of NcoI-HF, 2 µl of 10×NEB CutSmart buffer, and water to 20 µl. Genomic DNA digestions were incubated at 37° C. for approximately 16 hours. The digestions were submitted to 0.8% agarose gel electrophoresis using TAE buffer and blotted onto a hybond N+(GE Healthcare Life Sciences, Manchester, N.H., USA) using a TURBOBLOTTER® for approximately 1 hour following the manufacturer's recommendations. The membrane was hybridized with a 479 bp digoxigenin-labeled *Aspergillus niger* rlmA probe, which was synthesized by incorporation of digoxigenin-11-dUTP by PCR using primers HTJP-553 (sense) and HTJP-554 (antisense) shown below:

```
SEQ ID NO: 8:
Primer HTJP-553:
5' gctaaaggtgatggaactgc

SEQ ID NO: 9:
Primer HTJP-554:
5' gagtgacggtattttggagg
```

The amplification reaction (50 µl) was composed of 200 µM PCR DIG Labeling Mix (Roche Applied Science, Palo Alto, Calif., USA), 0.5 µM primers by KOD-Plus (TOYOBO) using pHiTe177 as template in a final volume of 50 µl. The amplification reaction was incubated in a Bio-Rad® C1000 Touch™ Thermal Cycler programmed for 1 cycle at 94° C. for 2 minutes; 30 cycles each at 94° C. for 15 seconds, 55° C. for 30 seconds, and 68° C. for 30 seconds and a 4° C. hold. PCR products were separated by 0.8% agarose gel electrophoresis using TAE buffer where a 0.5 kb fragment was excised from the gel and extracted using a QIAQUICK® Gel Extraction Kit. The denatured probe was added directly to the DIG Easy Hyb buffer and an overnight hybridization at 42° C. was done. Following the post hybridization washes (twice in 2× SSC, room temperature, 5 min and twice in 0.1×SSC, 68° C., 15 min. each), chemiluminescent detection using the DIG detection system and CPD-Star (Roche) was done followed by manufacture's protocol. The DIG-labeled DNA Molecular Weight Marker II (Roche) was used for the standard marker. The strains, 177-M1412-1 and 177-M1412-7, giving the correct integration at the rlmA loci (a hybridized band shifted from 2981 bp to 5236 bp) were selected for the subsequent experiments.

Example 2: Effect of the rlmA Gene Disruption on Glucoamylase Production

Two strains from M1412 were fermented in lab-scale tanks and their enzyme activities (AGU activities) were measured followed by the materials and methods described above; results are shown in the table below. The rlmA-disrupted strains showed around 1.2 times higher glucoamylase (AGU) activity than the reference rlmA-wildtype strain M1412 in jar fermenters.

TABLE 1

The average AGU activity of the selected three strains from each host strain, wherein the average Gs AMG yields from M1412 is normalized to 1.00.

| Strain | AGU relative activity |
|---|---|
| A. niger M1412 | 1.00 |
| A. niger 177-M1412-1 (ΔrlmA) | 1.19 |
| A. niger 177-M1412-7 (ΔrlmA) | 1.22 |

Example 3: Construction of Plasmids pHUda1260 and pIhar243

Materials and Methods
Plasmids
pBluescript II SK- (Stratagene #212206). The plasmid pRika147 is described in example 9 in WO2012160093. The sequence information for PLC harboring the phospholipase C from Kionochaeta sp. is disclosed in WO 2015/173426 (SEQ ID NO: 2).
Microbial Strains
The expression host strain *Aspergillus niger* C3085 was isolated by Novozymes and is a derivative of *Aspergillus niger* NN049184 which was isolated from soil described in example 14 in WO2012/160093. The strain 177-M1412-1 is described in Example 1 (NZ 14148-EP-EPA).
Medium
MSS is composed of 70 g Sucrose, 100 g Soybean powder (pH 6.0), water to 1 litre.
MU-1glu+Zn-Suc is composed 260 g of glucose, 3 g of $MgSO_4 \cdot 7H_2O$, 5 g of $KH_2PO_4$, 6 g of $K_2SO_4$, 23.6 g of succinic acid, amyloglycosidase trace metal solution 0.5 ml and 100 mM $ZnSO_4$ $7H_2O$ 1 ml and urea 2 g (pH 4.5), water to 1 litre.
Phopspholipase C Expression in Shake Flask Fermentation.
Shake flasks containing 100 ml of the seed medium MSS (70 g Sucrose, 100 g Soybean powder (pH 6.0), water to 1 litre) were inoculated with spores from the *A. niger* strain 127-C3085-16 and incubated at 30° C., with shaking (220 rpm) for 3 days. Ten ml of the seed culture was transferred to shake flasks containing 100 ml of the main medium MU-1glu+Zn-Suc and incubated at 30° C., with shaking (220 rpm) for 6 days. The culture supernatants were collected by centrifugation and used for sub-sequent assay.
PLC Activity
PLC activity was measured by following method.
pNPPC substrate solution: 5 mM p-Nitrophenylphosphorylcholine (Sigma), 50 mM NaOAc,
0.5 mM zinc sulfate, pH 4.75
Temperature: 30° C.
Assay buffer: 50 mM NaOAc, 0.5 mM zinc sulfate, 0.1% Triton™ X-100, pH 4.75\
Stop solution: 1M Tris-HCl, pH 8.5
Fifty ul of diluted PLC samples (The supernatants were diluted in Assay buffer) were prepared. The assay was then started by adding 50 µl of pNPPC substrate solution into the samples and the reaction mixture was incubated at 30° C. for 15 min. The reaction was terminated by adding 100 ul of stop solution. OD values are measured by microplate reader at 410 nm as the PLC activity.

Construction of pHUda1260

The plasmid pHUda1260 was constructed by changing from the *A. nidulans* orotidine-5'-phosphate decarboxylase gene (pyrG) to the *A. nidulans* acetamidase gene (amdS) in pRika147.

Plasmid pRika147 (described in example 9 in WO2012160093) was digested with SphI and SpeI, and its ends were filled-in by use of T4 DNA polymerase followed by manufacture's protocol (NEB, New England Biolabs, Inc.). The fragment was purified by 0.8% agarose gel electrophoresis using TAE buffer, where a 9,241 bp fragment was excised from the gel and extracted using a QIA-QUICK® Gel Extraction Kit.

Plasmid pHUda1019 (described in example 2 in WO2012160093) was digested with XbaI and AvrII, and its ends were filled-in by use of T4 DNA polymerase followed by manufacture's protocol (NEB, New England Biolabs, Inc.). The fragment was purified by 0.8% agarose gel electrophoresis using TAE buffer, where a 3,114 bp fragment containing amdS gene, *A. oryzae* tef1 (translation elongation factor 1) promoter and *A. oryzae* niaD (nitrate reductase) terminator was excised from the gel and extracted using a QIAQUICK® Gel Extraction Kit. The 9,241 bp fragment was ligated to the 3,114 bp fragment in a reaction composed of 1 µl of the 9,241 bp fragment, 3 µl of the 3,114 bp fragment, 1 µl of 5× ligase Buffer, 5 µl of 2× Ligase Buffer and 1 µl of Ligase (Roche Rapid DNA Ligation Kit). The ligation reaction was incubated at room temperature for 10 minutes. Five µl of the ligation mixture were transformed into DH5-alpha chemically competent *E. coli* cells. Transformants were spread onto LB plus ampicillin plates and incubated at 37° C. overnight. Plasmid DNA was purified from several transformants using a QIA mini-prep kit. The plasmid DNA was screened for proper ligation by use of proper restriction enzymes followed by 0.8% agarose gel electrophoresis using TAE buffer. One plasmid was designated as pHUda1260.

Construction of the PLC Gene Expression Plasmid PIhar243

The codon-optimized PLC gene from Kionochaeta sp. designed by Novozymes (SEQ ID NO:10) was synthesized by GeneArt™ services (Thermo Fisher Scientific). The coding region was amplified from the GeneArt plasmid with the primers (SEQ ID NOs: 11 and 12) and ligated by In-Fusion® HD Cloning Kit (Clontech Laboratories, Inc) into the pHUda1260 digested with BamHI and PmlI to create pIhar243.

```
SEQ ID NO: 11:
agtcttgatcggatccaccatgagggcctcctccatctt

SEQ ID NO: 12:
cgttatcgtacgcaccacgtgctaaacggccatccggcgtttc
```

Transformation of PLC Gene in *A. niger*

Chromosomal insertion into either *A. niger* C3085 or 177-M1412-1 of the PLC gene (pIhar243) with amdS selective marker was performed as described in WO 2012/160093. Strains which grew well were purified and subjected to southern blotting analysis to confirm whether the PLC gene in pHiTe243 was introduced at NA1, NA2, SP288 or PAY loci correctly or not. The following set of primers to make non-radioactive probe was used to analyze the selected transformants for the PLC coding region:

```
SEQ ID NO: 13 primer IH198:
gtcactgccgcgcttgctgc

SEQ ID NO: 14 primer HTJP-375:
ccgcacgtgctaaacggccatccggcgtttc
```

Genomic DNA extracted from the selected transformants was digested by SpeI and PmlI, then hybridized with a 334-bp digoxigenin-labeled PLC probe. By the right gene introduction event, hybridized signals at the size of 6.4 kb (NA1), 4.3 kb (NA2), 3.1 kb (SP288) and 5.3 kb (PAY) by SpeI and PmlI digestion was observed probed described above.

Among the strains given the right integration events of 4-copies of the genes at NA1, NA2, SP288 and PAY loci, one strain with the Kionochaeta PLC from C3085 (+rlmA) was selected and designated as C3294. Three strains with the Kionochaeta PLC from 177-M1412-1 (ΔrlmA) were selected and designated as 169-C4572-1, 169-C4572-3 and 169-C4572-5.

Example 4 Effect of the rlmA Gene Deletion on Phospholipase C Production

Shaking flasks fermentation was done on the selected strains as described in materials and methods. Selected strains were pre-cultured in seed media then grown mycelia were transferred to the main medium for further cultivation of enzyme production. Cultivation was done at 30° C. for 6 days. Culture supernatants after centrifugation were used for enzyme assay.

As anticipated, the rlmA-disrupted strains showed around 1.2-times higher PLC activity than the reference rlmA-wildtype strain C3294 under the conditions.

TABLE 2

The average PLC activity of the selected strains from each host strain, wherein the average PLC yields from C3294 (reference) is normalized to 1.00.

| Strain | PLC relative activity |
|---|---|
| *A. niger* C3294 (+rlmA) | 1.00 |
| *A. niger* 169-C4572-1 (ΔrlmA) | 1.18 |
| *A. niger* 169-C4572-3 (ΔrlmA) | 1.23 |
| *A. niger* 169-C4572-5 (ΔrlmA) | 1.16 |

The invention claimed is:

1. An *Aspergillus* host cell comprising a heterologous polynucleotide encoding a secreted polypeptide of interest and comprising an inactivated rImA gene or homologue thereof, wherein said rImA gene or homologue thereof encodes an RImA polypeptide having at least 80% amino acid sequence identity with SEQ ID NO:3.

2. The host cell of claim 1, wherein the secreted polypeptide of interest is an enzyme.

3. The host cell of claim 1, wherein the rImA gene or homologue thereof comprises or consists of a genomic nucleotide sequence at least 80% identical to the genomic DNA sequence shown in SEQ ID NO: 1.

4. The host cell of claim 1, wherein the rImA gene or homologue thereof comprises or consists of a genomic nucleotide sequence, the cDNA sequence of which is at least 80% identical to the cDNA sequence shown in SEQ ID NO: 2.

5. A method of producing a secreted polypeptide of interest, said method comprising the steps of:
a) cultivating an *Aspergillus* host cell comprising a heterologous polynucleotide encoding the secreted polypeptide of interest and comprising an inactivated rImA gene or homologue thereof under conditions conducive to the expression of the secreted polypeptide of interest, wherein said rImA gene or homologue thereof encodes an RImA polypeptide having at least 80% amino acid sequence identity with SEQ ID NO: 3; and, optionally,
b) recovering the secreted polypeptide of interest.

6. The method of claim 5, wherein the secreted polypeptide of interest is an enzyme.

7. The method of claim 5, wherein the rImA gene or homologue thereof comprises or consists of a genomic nucleotide sequence at least 80% identical to the genomic DNA sequence shown in SEQ ID NO: 1.

8. The method of claim 5, wherein the rImA gene or homologue thereof comprises or consists of a genomic nucleotide sequence, the cDNA sequence of which is at least 80% identical to the cDNA sequence shown in SEQ ID NO: 2.

9. A method of producing an *Aspergillus* host cell having an improved yield of a secreted heterologous polypeptide of interest, said method comprising the following steps in no particular order:
a) transforming a filamentous fungal host cell with a heterologous polynucleotide encoding the secreted polypeptide of interest; and
b) inactivating an rImA gene or a homologue thereof in the filamentous fungal host cell, wherein said rImA gene or a homologue thereof encodes an RImA polypeptide having at least 80% amino acid sequence identity with SEQ ID NO: 3.

10. The method of claim 9, wherein the secreted polypeptide of interest is an enzyme.

11. The method of claim 9, wherein the rImA gene or homologue thereof comprises or consists of a genomic nucleotide sequence at least 80% identical to the genomic DNA sequence shown in SEQ ID NO: 1.

12. The method of claim 9, wherein the rImA gene or homologue thereof comprises or consists of a genomic nucleotide sequence, the cDNA sequence of which is at least 80% identical to the cDNA sequence shown in SEQ ID NO: 2.

13. The host cell of claim 1, wherein the *Aspergillus* cell is an *Aspergillus awamori, Aspergillus foetidus, Aspergillus fumigatus, Aspergillus japonicus, Aspergillus nidulans, Aspergillus niger*, or *Aspergillus oryzae* cell.

14. The host cell of claim 2, wherein the enzyme is a hydrolase, isomerase, ligase, lyase, oxidoreductase, or transferase.

15. The host cell of claim 2, wherein the enzyme is an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

16. The host cell of claim 1, wherein the RImA polypeptide comprises or consists of an amino acid sequence at least 85% identical to the amino acid sequence shown in SEQ ID NO: 3.

17. The host cell of claim 1, wherein the RImA polypeptide comprises or consists of an amino acid sequence at least 90% identical to the amino acid sequence shown in SEQ ID NO: 3.

18. The host cell of claim 1, wherein the RImA polypeptide comprises or consists of an amino acid sequence at least 95% identical to the amino acid sequence shown in SEQ ID NO: 3.

19. The method of claim 5, wherein the *Aspergillus* cell is an *Aspergillus awamori, Aspergillus foetidus, Aspergillus fumigatus, Aspergillus japonicus, Aspergillus nidulans, Aspergillus niger*, or an *Aspergillus oryzae* cell.

20. The method of claim 6, wherein the enzyme is a hydrolase, isomerase, ligase, lyase, oxidoreductase, or transferase.

21. The method of claim 6, wherein the enzyme is an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

22. The method of claim 5, wherein the RImA polypeptide comprises or consists of an amino acid sequence at least 85% identical to the amino acid sequence shown in SEQ ID NO: 3.

23. The method of claim 5, wherein the RImA polypeptide comprises or consists of an amino acid sequence at least 90% identical to the amino acid sequence shown in SEQ ID NO: 3.

24. The method of claim 5, wherein the RImA polypeptide comprises or consists of an amino acid sequence at least 95% identical to the amino acid sequence shown in SEQ ID NO: 3.

25. The method of claim 10, wherein the enzyme is a hydrolase, isomerase, ligase, lyase, oxidoreductase, or transferase.

26. The method of claim 10, wherein the enzyme is an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

27. The method of claim 9, wherein the RImA polypeptide comprises or consists of an amino acid sequence at least 85% identical to the amino acid sequence shown in SEQ ID NO: 3.

28. The method of claim 9, wherein the RImA polypeptide comprises or consists of an amino acid sequence at least 90% identical to the amino acid sequence shown in SEQ ID NO: 3.

29. The method of claim 9, wherein the RImA polypeptide comprises or consists of an amino acid sequence at least 95% identical to the amino acid sequence shown in SEQ ID NO: 3.

30. The host cell of claim 9, wherein the *Aspergillus* cell is an *Aspergillus awamori, Aspergillus foetidus, Aspergillus fumigatus, Aspergillus japonicus, Aspergillus nidulans, Aspergillus niger*, or *Aspergillus oryzae* cell.

* * * * *